(12) United States Patent
Hille

(10) Patent No.: US 6,344,211 B1
(45) Date of Patent: *Feb. 5, 2002

(54) TRANSDERMAL ABSORPTION OF ACTIVE SUBSTANCES FROM SUBCOOLED MELTS

(75) Inventor: Thomas Hille, Neuwied (DE)

(73) Assignee: LTS Lohmann Therapie-Systeme GmbH, Neuwied (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/716,442

(22) Filed: Nov. 21, 2000

Related U.S. Application Data

(63) Continuation of application No. 09/436,717, filed on Nov. 9, 1999, now abandoned, which is a continuation of application No. 08/860,961, filed as application No. PCT/EP95/05006 on Dec. 18, 1995, now Pat. No. 6,264,980.

(30) Foreign Application Priority Data

Dec. 24, 1994 (DE) .......................................... 44 46 600

(51) Int. Cl.⁷ ................................................ A61F 13/00
(52) U.S. Cl. ...................... 424/449; 424/447; 514/946; 514/567
(58) Field of Search ............................... 424/447, 448, 424/449; 514/946, 567

(56) References Cited

U.S. PATENT DOCUMENTS

| | | | |
|---|---|---|---|
| 3,598,122 A | 8/1971 | Zaffaroni | 129/268 |
| 4,900,730 A | 2/1990 | Miyauchi | 514/12 |
| 5,240,711 A | * 8/1993 | Hille et al. | 424/448 |

FOREIGN PATENT DOCUMENTS

| | | |
|---|---|---|
| DE | 3 315 272 | 10/1984 |
| DE | 3 843 239 | 2/1990 |
| EP | 0430019 | 6/1991 |
| JP | 58-124711 | 7/1983 |
| WO | 91/04733 | 4/1991 |
| WO | 91/19474 | 12/1991 |

* cited by examiner

*Primary Examiner*—Thurman K. Page
*Assistant Examiner*—Lakshmi Channavajjala
(74) *Attorney, Agent, or Firm*—Wenderoth, Lind & Ponack, L.L.P.

(57) ABSTRACT

A pharmaceutical product for the release of medicinal agents to the skin having absorption-increasing auxiliary agents is characterized in that the auxiliary material forms subcooled melts.

6 Claims, No Drawings

TRANSDERMAL ABSORPTION OF ACTIVE SUBSTANCES FROM SUBCOOLED MELTS

This application is a continuation of Ser. No. 09/436,717 filed Nov. 9, 1999, now abandoned, which is a continuation of Ser. No. 08/860,961 filed Nov. 7, 1997, now U.S. Pat. No. 6,264,980, which is a 371 of PCT/EP95/05006 filed Dec. 18, 1995.

The present invention relates to the transdermal application of medicinal agents with the aid of inactive ingredients forming sub-cooled melts. Applying pharmaceuticals transdermally undoubtedly is very advantageous, but the limited quantity of medicinal substance that can be absorbed by the skin frequently is a disadvantage. With introducing the therapy by means of transdermal application there have therefore been attempts to increase the pharmaceuticals' capability of penetrating through the skin. The development of penetration enhancers added to drugs for dermal application is regarded as one approach. These substances change subjacent skin structures, at least for a short period; in unfavorable cases they may result in undesired side effects. These side effects are the less marked, the better the penetration enhancers are tolerated physiologically.

A neat approach of increasing the absorption of medicinal agents through the skin is the manufacture of matrix systems. Owing to the concentration gradient the dissolved portion of the active substance diffuses out of the system into the skin first. At the same time, the portion of active substance which is contained in the system in suspended form starts to dissolve. The dissolution rate of the active substance in the system is the factor determining the rate of active substance release. Experiments have shown that dodecanol promotes penetration and is physiologically acceptable. Since its melting point amounts to about 24° C. dodecanol is solid at normal room temperature. The solid state makes it more difficult to deliver dodecanol out of a matrix. This deficiency restricts the use of dodecanol in polymeric matrices because the release rate of a substance from polymer matrices is the higher, easier it can diffuse, in as the matrix. This does not only apply to dodecanol, but also to other penetration enhancers which are solid at room temperature.

Accordingly it is the object of the present invention to improve the release of auxiliary agents which are solid at room temperature from a matrix.

Most surprisingly, this object has been achieved according to the present invention by a pharmaceutical product as defined herein. Compounds forming subcooled melts are understood to mean those whose melting point is above room temperature but which, after a melting process, remain in the liquid state during cooling to room temperature.

The term drug is known to the skilled artisan. Ointments representing gels of plastic deformability as well as pastes which may be characterized as ointments having a high solids content are suitable for the application to the skin or mucous membranes (e.g. nose, eye).

A transdermal therapeutic system (TTS) is to be understood according to Zaffaroni as "a medicinal substance-containing device or administration form continuously releasing one or several medicinal agents at a predetermined rate over a predetermined period of time to a fixed place of application" (quoted according to Heilmann, therapeutische Systeme—Konzept und Realisation programmierter Arzneiverabreichung, 4th edition, Ferdinand Enke Verlag, Stuttgart 1984, page 26). In the present case the place of application is the skin.

The structure of transdermal systems is known to the skilled artisan. Patents describing the basic design include, for example, DE 3315272, DE 3843239, U.S. Pat. No. 3,598,122.

When a transdermal therapeutic system is applied on the skin of a patient, the medicinal agent is to be released to take a topical or systemic effect in the patient. Administration forms of this kind have already been used in therapy. In most cases they have a layered structure; in the simplest case they consist of a backing layer, a self-adhesive active substance reservoir, and a removable protective layer to be removed prior to application. In the present case, an auxiliary agent must be introduced that increases the absorption of medicinal agents by the skin, is solid at room temperature, and forms subcooled melts, for example, dodecanol or levulic acid.

Substances are used as medicinal agents which—when applied on the skin either without or with an absorption filter—produce a local or systemic effect.

Substances having a local action include, for example, antiperspirants, fungicides, bactericides, and bacteriostatics.

Substances having a systemic action include, for example, antibiotics, hormones, antipyretics, antidiabetic agents, coronary vasodilators, cardio-active glycosides, analgesics, spasmolytics, antihypertensives, psychotropic drugs, migraine analgesics, corticoids, contraceptives, antirheumatics, anticholinergics, sympathicolytics, sympathicomimetics, vasodilators, anticoagulants, and antiarrhythmics. This listing is incomplete.

The delivery of pilocarpine base and ephedrine base from polymer matrices can also be increased, provided that they are present in subcooled melts. Owing to their heat-sensitivity, however, it is impossible to subject these medicinal substances to a melting process.

The present invention will be illustrated by the following Examples:

EXAMPLE 1

1,139 g of a 47.83%-wt. polyacrylate solution of a self-crosslinked acrylate copolymer of 2-ethylhexyl acrylate, vinyl acetate, acrylic acid, (solvent: ethyl acetate:heptane:isopropanol:toluene:acetylacetonate in the ratio of 37:26:26:4:1), 100 g of levulic acid, 150 g of oleyl oleate, 100 g of polyvinylpyrrolidone, 150 g of ethanol, 200 g of ethyl acetate, and 100 g of buprenorphine base are homogenized. The mixture is stirred for about 2 hours; and dissolution of all solids is controlled visually. The evaporation logs is controlled by reweighing, the possible solvent loss is replenished by ethyl acetate.

Subsequently, the mixture is applied on a transparent polyester film of 420 mm in width in such a manner that the mass per unit area of the dry adhesive layer amounts to about 80 g per m$^2$. The polyester film rendered removable by means of siliconization serves as protective layer.

The solvents are removed by drying with heated air which is guided over the moist web. The heat treatment results in evaporation of the solvents, but also in melting of the levulic acid. Afterwards the adhesive film is covered with a polyester film of 15μ. An area of 16 cm$^2$ is punched by means of suitable cutting tools, and the edges left between the individual systems are removed. Examples 2 to 5 were conducted in accordance with Example 1.

Column 1 indicates the number of the experiment, column 2 the concentration of buprenorphine base, column 3 the quality and quantity of the acid used, column 4 the dissociation constant of the acids used, column 5 the plasticizer, column 6 the polymers used, and column 7 the absorption rate under in-vitro-conditions. The relative amount of buprenorphine base diffusing through mice skin within 24 h, relative to the amount per TTS, is given. The penetration results were obtained using mice skin clamped in a Franz-Cell. The composition of Examples 2–5 are shown in Table 1.

The results of the in-vitro-penetration tests and the qualitative and quantitative compositions of buprenorphine-TTS according to Examples 1–5 are represented in Table 1:

TABLE 1

Flux of buprenorphine base from TTSs having different acids

| Example | Buprenorphine base | Acid | $pK_a$ value | Plasticizer | Polymers | Penetration [%] buprenorphine base relative to the amount of medicinal agent in TTS |
|---|---|---|---|---|---|---|
| 1 | 10% | 10% glutaric acid monomethyl ester | 4.33* | cetiol 10% | dry polyacrylate 70% | 28.6 |
| 2 | 10% | 15% octanoic acid | 4.85 | cetiol 10% | dry polyacrylate 55% PVP 10% | 5.9 |
| 3 | 10% | 10% levulic acid | 4.4** | cetiol 10% | dry polyacrylate 60% PVP 10% | 38.6 |
| 4 | 10% | 15% undecenoic acid DAB 10 | 4.5 | cetiol 10% | dry polyacrylate 55% PVP 10% | 7.7 |
| 5 | 10% | undecenoic 10% | 4.5 | dodecanol 10% | dry polyacrylate | 27.3 |

*$pK_a$ I of glutaric acid
**determined by experiment
Cetiol = oleyl oleate DAB 10
PVP = polyvinylpyrrolidone DAC It is seen from column 4 that the dissociation constants of the carboxylic acids used are quite similar. However, if the plasticizer, oleyl oleate, is used in a 10%-concentration each time, it can be seen from Examples 1 and 3 or 2 and 4 that only the carboxylic acids having a tendency to form sub-cooled melts cause a marked penetration increase under in-vitro conditions. As can be seen from the dissociation constants, undecenoic acid and octanoic acid are weaker acids than glutaric acid monomethyl ester or levulic acid. This was compensated by a higher concentration of the two weaker acids, amounting to 15%, as compared to the concentration of the two stronger acids. However, it can also be seen that the dissociation constants are so similar that the absorption-promoting effect cannot be explained by the dissociation constants. Example 5 demonstrates that it is possible to increase the absorption even with an acid which obviously has an only slight effect on the penetration promotion of buprenorphine base, if a neutral substance, that is dodecanol, is used which forms sub-cooled melts like levulic acid or glutaric acid monomethyl ester do. The physical effect of the specified adjuvants is sufficiently proved by the five Examples.

Recrystallization of levulic acid or dodecanol during storage did not occur in any of the samples, even if the storage temperature amounted to 4° C.

What is claimed is:

1. A method of releasing a pharmaceutical agent for effecting a topical or systemic effect in a patient from a transdermal therapeutic system having a layered structure and comprising at least one substance selected from the group of pharmaceutical agents producing a local or systemic effect and at least one auxiliary agent which increases the penetration of said pharmaceutical agents and has a melting point above room temperature, which comprises:

a) in a first step preparing said transdermal therapeutic system by using an auxiliary agent which has been melted and afterwards allowed to form a subcooled melt by cooling it down to room temperature, and b) in a second step applying the transdermal therapeutic system as prepared in the first step on the skin of said patient.

2. The method according to claim 1, wherein the pharmaceutical agent producing a local effect is a member selected from the group consisting of antiperspirants, fungicides, bactericides, and bacteriostatics.

3. The method according to claim 1, wherein the pharmaceutical agent producing a systemic effect is a member selected from the group consisting of antibiotics, hormones, antipyretics, antidiabetic agents, coronary vasodilators, cardioactive glycosides, analgetics, spasmolytics, antihypertensives, psychotropic drugs, migraine analgesics, corticoids, contraceptives, antirheumatics, anticholinergics, symphaticolytics, symphaticomimetics, vasodilators, anticoagulants, and antiarrhytmics.

4. The method according to claim 1, wherein the pharmaceutical agent producing a systemic effect is a member selected from the group consisting of buprenorphine base, pilocarpine base, and ephedrine base.

5. The method according to claim 1, wherein the pharmaceutical agent is buprenorphine base and the auxiliary agent is selected from the group consisting of levulic acid, glutaric acid monomethyl ester and dodecanol.

6. The method according to claim 1, wherein the pharmaceutical agent is buprenorphine base and the auxiliary agent is levulic acid.

* * * * *